United States Patent
Martin et al.

(10) Patent No.: US 9,387,032 B2
(45) Date of Patent: Jul. 12, 2016

(54) SYSTEMS AND METHODS FOR DETECTING CHANNEL FAULTS IN ENERGY DELIVERY SYSTEMS

(75) Inventors: Gregory James Martin, Carlsbad, CA (US); Duane Ellis Tumlinson, San Clemente, CA (US)

(73) Assignee: Medtronic Ablation Frontiers LLC, Minneapolis, MN (US)

(*) Notice: Subject to any disclaimer, the term of this patent is extended or adjusted under 35 U.S.C. 154(b) by 971 days.

(21) Appl. No.: 13/525,472

(22) Filed: Jun. 18, 2012

(65) Prior Publication Data
US 2013/0336356 A1    Dec. 19, 2013

(51) Int. Cl.
*G01K 3/04* (2006.01)
*G01K 7/02* (2006.01)
*A61B 18/12* (2006.01)
*A61B 18/00* (2006.01)

(52) U.S. Cl.
CPC ......... *A61B 18/1206* (2013.01); *A61B 18/1233* (2013.01); *A61B 2018/00666* (2013.01); *A61B 2018/00821* (2013.01)

(58) Field of Classification Search
CPC ......... G01K 7/04; G01K 7/026; G01K 13/00; G01K 1/08; G01K 3/04; G01K 7/02; A61B 2018/00791; A61B 2017/00084; A61B 2018/0016; A61B 2018/00821
USPC ......... 374/179, 163, 141, 208, 183, 100–102, 374/1; 702/130, 131, 99; 136/200, 224
See application file for complete search history.

(56) References Cited

U.S. PATENT DOCUMENTS

| | | | | |
|---|---|---|---|---|
| 4,297,685 A | * | 10/1981 | Brainard, II | A61B 5/01 340/573.1 |
| 4,616,485 A | * | 10/1986 | Gillett | B60H 1/3225 165/11.1 |
| 5,663,899 A | | 9/1997 | Zvonar et al. | |
| 5,957,969 A | | 9/1999 | Warner et al. | |

(Continued)

FOREIGN PATENT DOCUMENTS

| | | |
|---|---|---|
| EP | 1280467 B1 | 11/2008 |
| EP | 2338431 A1 | 12/2010 |

(Continued)

OTHER PUBLICATIONS

International Search Report dated Sep. 17, 2013 for International Application Serial No. PCT/US2013043816, International Filing Date Jun. 3, 2013 consisting of 3 pages.

(Continued)

*Primary Examiner* — Gail Kaplan Verbitsky
(74) *Attorney, Agent, or Firm* — Christopher & Weisberg, P.A.

(57) ABSTRACT

A method of detecting a thermocouple short circuit in a medical device, including obtaining a first temperature measurement from a thermocouple of the medical device; obtaining a second temperature measurement from the thermocouple; calculating a rate of change over time between the first and second temperature measurements; comparing the calculated rate of change over time to a predefined rate of change over time threshold; and generating an indication of a thermocouple short circuit based at least in part on the comparison.

10 Claims, 4 Drawing Sheets

(56) References Cited

U.S. PATENT DOCUMENTS

| | | | |
|---|---|---|---|
| 6,441,350 B1* | 8/2002 | Stoddard | C23C 16/52 219/486 |
| 7,008,417 B2 | 3/2006 | Eick | |
| 7,841,771 B2* | 11/2010 | Perotti et al. | 374/179 |
| 8,057,465 B2 | 11/2011 | Sliwa, Jr. et al. | |
| 8,119,981 B2* | 2/2012 | Powell | 250/281 |
| 2005/0015125 A1 | 1/2005 | Mioduski et al. | |
| 2006/0042278 A1* | 3/2006 | Ludwig et al. | 62/130 |
| 2007/0203481 A1 | 8/2007 | Gregg et al. | |
| 2010/0087810 A1 | 4/2010 | Odell et al. | |
| 2010/0204694 A1* | 8/2010 | Mehta et al. | 606/42 |
| 2011/0270247 A1 | 11/2011 | Sherman | |

FOREIGN PATENT DOCUMENTS

| | | |
|---|---|---|
| EP | 1450712 B1 | 5/2011 |
| WO | 2008141104 A2 | 11/2008 |
| WO | 2011080666 A1 | 7/2011 |

OTHER PUBLICATIONS

Written Opinion of the International Searching Authority dated Sep. 17, 2013 for International Application Serial No. PCT/US2013043816, International Filing Date Jun. 3, 2013 consisting of 5 pages.

* cited by examiner

SYSTEMS AND METHODS FOR DETECTING CHANNEL FAULTS IN ENERGY DELIVERY SYSTEMS

CROSS-REFERENCE TO RELATED APPLICATION n/a

STATEMENT REGARDING FEDERALLY SPONSORED RESEARCH OR DEVELOPMENT n/a

FIELD OF THE INVENTION

Systems and methods for detecting channel faults or electrical shorts in energy delivery systems used to treat tissue, and more particularly, systems and methods for detecting electrical shorts between sensors in a medical treatment energy delivery system.

BACKGROUND OF THE INVENTION

Thermal tissue treatments are employed for a variety of different medical conditions. For example, radiofrequency (RF) and cryogenic ablation procedures are well recognized treatments for vascular and cardiac diseases such as atrial fibrillation, as well as for ablative treatment of cancerous tissue and other physiological conditions. The application of either RF or cryogenic treatment is usually based on the preference of the surgeon or the specific tissue to be treated. In either RF or cryogenic ablation, however, the location and quality of the lesion produced is a primary concern. The clinical success of a particular tissue ablation procedure depends on efficacy and safety of the application of the selected energy. Many factors influence lesion size such as tissue-electrode contact force, ablation energy level, and cooling factors, that is, blood flow rate, tissue perfusion, and the duration of energy delivery. Fast and accurate temperature acquisition can provide an important metric in delivering the proper amount of diagnostic and/or treatment energy to a tissue site. For example, the delivery of excessive energy in cardiac procedures can cause coagulum and/or damage adjacent tissues and structures such as the phrenic nerve or the esophagus of the patient. Insufficient energy delivery can result in poor lesion creation and low therapeutic success rates. Accordingly, thermocouples are often employed in proximity to a treatment region to provide the desired feedback to regulate power delivery.

However, during operation, thermocouples within a medical device may short-circuit. Shorts can be caused by a breakdown in the insulative barrier between individual conductors intended to be isolated. In addition, shorts can occur not only between multiple thermocouples, but also within a thermocouple consisting of a pair of wires. A thermocouple short circuit may be indicated by temperature variations between one or more thermocouples, but such temperature variations could also result from a change in blood flow or tissue contact with the medical device where the thermocouples are mounted. Accordingly, it may be difficult to distinguish between an actual short-circuit or channel fault of a particular thermocouple and a change in the physiological condition or environment of the medical device.

SUMMARY OF THE INVENTION

A method of detecting a thermocouple short circuit in a medical device is disclosed, including obtaining a first temperature measurement from a thermocouple of the medical device; obtaining a second temperature measurement from the thermocouple; calculating a rate of change over time between the first and second temperature measurements; comparing the calculated rate of change over time to a predefined rate of change over time threshold; and generating an indication of a thermocouple short circuit based at least in part on the comparison. The second temperature measurement may be obtained within approximately 200 milliseconds or less of the first temperature measurement. The predefined rate of change over time threshold may be approximately 15 degrees per second or more. The method may include comparing at least one of the first and second temperature measurements to a predefined temperature threshold; and generating an indication of a thermocouple short circuit based at least in part on the comparison. The method may include delivering energy to the medical device; and modifying the energy delivery based at least in part on the comparison. The energy may include at least one of radiofrequency energy, electroporation energy, ultrasound energy, microwave and/or cryogenic energy. The generated indication may include at least one of an audible, visual, and tactile alert.

A method of detecting a thermocouple short circuit in a medical device is disclosed, including providing a medical device having a plurality of electrodes and at least one thermocouple coupled to each electrode; delivering energy to each of the plurality of electrodes; obtaining a first temperature measurement from the at least one thermocouple of each electrode; obtaining a second temperature measurement from the at least one thermocouple of each electrode; calculating a rate of change over time between the first and second temperature measurements; comparing the calculated rate of change over time to a predefined rate of change over time threshold; and generating an indication of a thermocouple short circuit based at least in part on the comparison. The method may include modifying the energy delivery based at least in part on the comparison. The medical device may include at least two thermocouples coupled to each electrode, where the first and second temperature measurements are obtained from a first thermocouple of the at least two thermocouples, and the method further includes obtaining a third temperature measurement from a second thermocouple of the at least two thermocouples; and comparing the third temperature measurement to a predefined temperature threshold.

A medical treatment system is disclosed, including a medical device having an electrode and a thermocouple coupled to the electrode; a control unit coupled to the electrode and the thermocouple, the control unit programmed to: obtain a first temperature measurement from the thermocouple; obtain a second temperature measurement from the thermocouple; calculate a rate of change over time between the first and second temperature measurements; compare the calculated rate of change over time to a predefined rate of change over time threshold; and generate an indication of a thermocouple short circuit based at least in part on the comparison. The control unit may be programmed to deliver energy to the electrode; and modify the energy delivery based at least in part on the comparison. The second temperature measurement may be obtained within approximately 200 milliseconds or less of the first temperature measurement, and the predefined rate of change over time threshold may be approximately 15 degrees per second or more.

A medical treatment system is disclosed, including a medical device having a plurality of electrodes, and at least two thermocouples in proximity to each electrode; a control unit coupled to the plurality of electrodes and the at least two thermocouples, the control unit programmed to: obtain a first temperature measurement from a first thermocouple of the at least two thermocouples of each electrode; obtain a second temperature measurement from the first thermocouple; calculate a rate of change over time between the first and second temperature measurements; compare the calculated rate of change over time to a predefined rate of change over time threshold; and generate an indication of a thermocouple short circuit based at least in part on the comparison. The control unit may be programmed to: obtain a third temperature measurement from a second thermocouple of the at least two thermocouples of each electrode; and compare the third temperature measurement to a predefined temperature threshold, wherein the indication of a thermocouple short circuit is generated based at least in part on this comparison. The control unit may be programmed to: deliver energy to the electrode; and modify the energy delivery based at least in part on the comparison, where modifying the energy delivery includes terminating energy delivery to at least one electrode.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
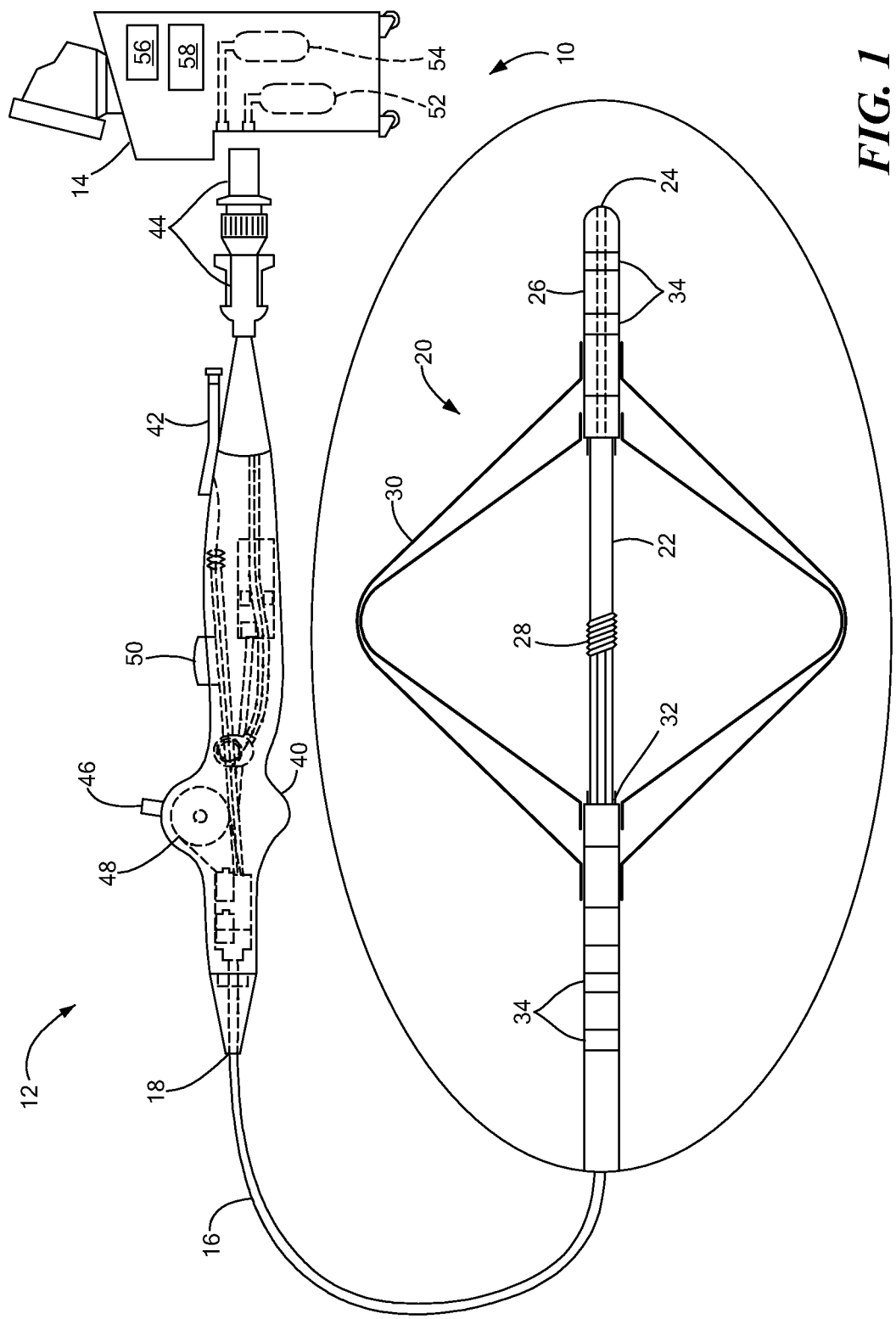
FIG. 1 is an illustration of an example of a medical system constructed in accordance with the principles of the present invention.
Figure 2:
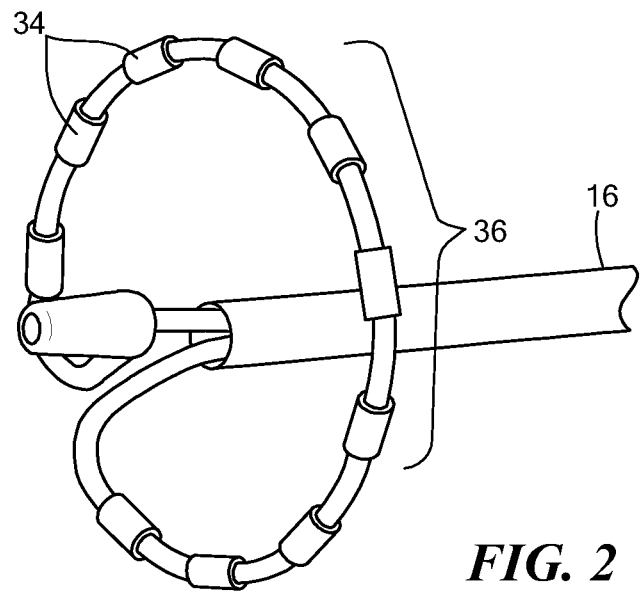
FIG. 2 is an illustration of an example of a medical device assembly constructed in accordance with the principles of the present invention.

The present invention advantageously provides systems and methods for detecting channel faults or electrical shorts in energy delivery systems used to treat tissue, and more particularly, systems and methods for detecting electrical shorts between sensors in a medical treatment energy delivery system. Referring now to the drawing figures in which like reference designations refer to like elements, an embodiment of a medical system constructed in accordance with principles of the present invention is shown in FIG. 1 and generally designated as "10." The system 10 generally includes a medical device 12 that may be coupled to a control unit 14 or operating console. The medical device 12 may generally include one or more diagnostic or treatment regions for energetic, therapeutic and/or investigatory interaction between the medical device 12 and a treatment site. The treatment region(s) may deliver, for example, cryogenic therapy, radiofrequency energy, electroporation energy, microwave energy, resistive heating energy, or other energetic transfer with a tissue area in proximity to the treatment region(s), including cardiac tissue.

Now referring to FIG. 1, the medical device 12 may include an elongate body 16 passable through a patient's vasculature and/or proximate to a tissue region for diagnosis or treatment, such as a catheter, sheath, or intravascular introducer. The elongate body 16 may define a proximal portion 18 and a distal portion 20, and may further include one or more lumens disposed within the elongate body 16 thereby providing mechanical, electrical, and/or fluid communication between the proximal portion of the elongate body 16 and the distal portion of the elongate body 16, as discussed in more detail below.

The medical device 12 may include a shaft 22 at least partially disposed within a portion of the elongate body 16. The shaft 22 may extend or otherwise protrude from a distal end of the elongate body 16, and may be movable with respect to the elongate body 16 in longitudinal and rotational directions. That is, the shaft 22 may be slidably and/or rotatably moveable with respect to the elongate body 16. The shaft 22 may further define a lumen 24 therein for the introduction and passage of a guide wire. The shaft 22 may include or otherwise be coupled to a distal tip 26 that defines an opening and passage therethrough for the guide wire.

The medical device 12 may further include a fluid delivery conduit 28 traversing at least a portion of the elongate body and towards the distal portion. The delivery conduit 28 may be coupled to or otherwise extend from the distal portion of the elongate body 16, and may further be coupled to the shaft 22 and/or distal tip of the medical device 12. The fluid delivery conduit 28 may define a lumen therein for the passage or delivery of a fluid from the proximal portion of the elongate body 16 and/or the control unit 14 to the distal portion and/or treatment region of the medical device 12. The fluid delivery conduit 28 may further include one or more apertures or openings therein, to provide for the dispersion or directed ejection of fluid from the lumen to an environment exterior to the fluid delivery conduit 28.

The medical device 12 may further include one or more expandable elements 30 at the distal portion of the elongate body 16. The expandable element 30 may be coupled to a portion of the elongate body 16 and also coupled to a portion of the shaft 22 and/or distal tip 26 to contain a portion of the fluid delivery conduit 28 therein. The expandable element 30 defines an interior chamber or region that contains coolant or fluid dispersed from the fluid delivery conduit 28, and may be in fluid communication with an exhaust lumen 32 defined by or included in the elongate body 16 for the removal of dispersed coolant from the interior of the expandable element 30. The expandable element 30 may further include one or more material layers providing for puncture resistance, radiopacity, or the like.

The medical device 12 may further include one or more electrically-conductive segments or electrodes 34 positioned on or about the elongate body for conveying an electrical signal, current, or voltage to a designated tissue region and/or for measuring, recording, or otherwise assessing one or more electrical properties or characteristics of surrounding tissue. The electrodes 34 may be configured in a myriad of different geometric configurations or controllably deployable shapes, and may also vary in number to suit a particular application, targeted tissue structure or physiological feature. For example, as shown in FIG. 1, the electrodes 34 may include a first pair proximate to the expandable element and a second electrode pair distal to the expandable element.

Alternative electrode configurations of the medical device 12 are illustrated in FIGS. 2-5. For example, FIG. 2 includes an electrode array 36 configurable into a looped or substantially circular configuration. Each electrode may be constructed of a conductive material, such as platinum or gold, and have a mass between 20 and 50 milligrams. Each electrode 34 may include one or more thermocouples 37 integral to or otherwise coupled to each electrode 34 and proximate a tissue contacting surface of the electrodes 34. As shown in FIG. 6, the thermocouples 37 may be positioned directly on a surface of the electrode, and may be spaced apart circumferentially and/or longitudinally along the length or width of the electrode 34. Alternatively, the thermocouples 37 may be positioned in proximity to the electrode, but not in direct thermal contact with the electrode 34. One or more wires (not shows) may be coupled to each thermocouple 37 to provide signals and/or communication with other components of the system. The electrode array 36 may be selectively adjustable to transition between a near-linear geometry to the near-helical geometry shown in FIG. 2.

Figure 3:
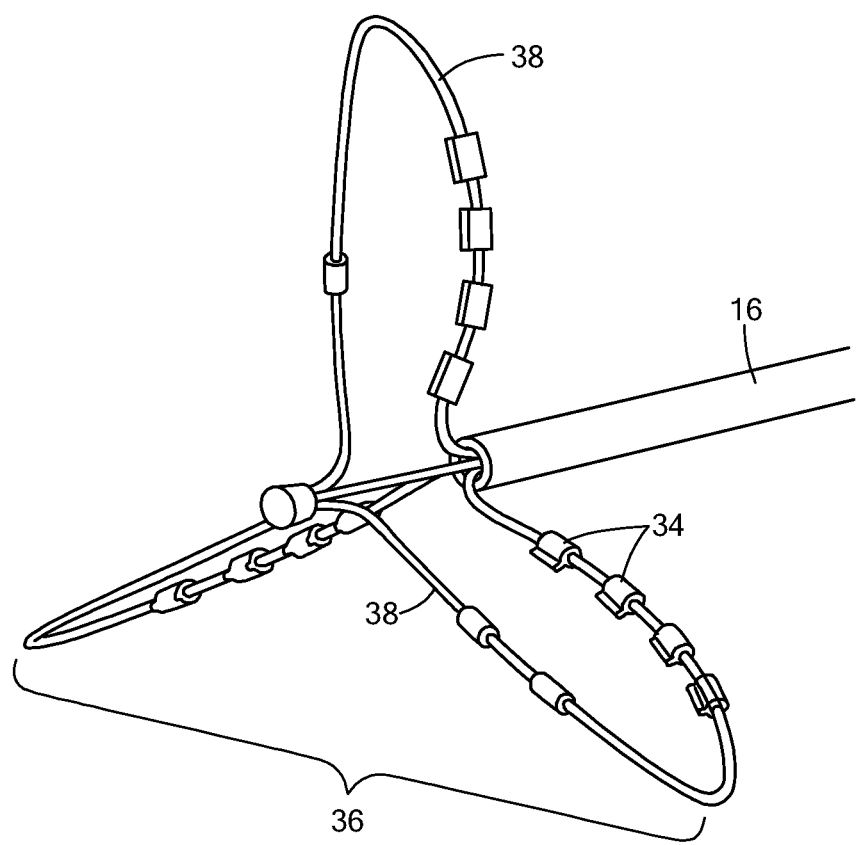
FIG. 3 is another illustration of an example of a medical device assembly constructed in accordance with the principles of the present invention.

The electrode array 36 in FIG. 3 includes a plurality of arms 38 arranged in an umbrella-like configuration, with the electrodes 34 positioned in a proximal-facing direction or orientation on the arms 38. The tissue contacting portion of electrodes 34 face toward the proximal end of the medical device such that pulling the electrode array 36 advances the tissue contacting portion of electrodes 34 into tissue. The electrode array 36 may be adjusted to transition between a near-linear geometry to the umbrella geometry shown in FIG. 3, which may be configured for contacting the septum of the left atrium of the heart of a patient.

Figure 4:
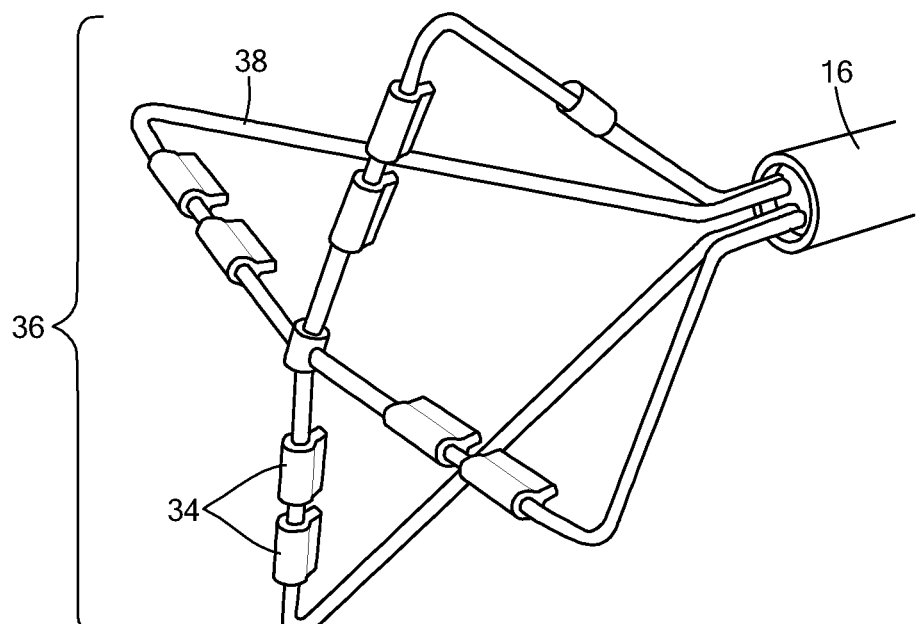
FIG. 4 is still another illustration of an example of a medical device assembly constructed in accordance with the principles of the present invention.

FIG. 4 also includes a plurality of extendable or deployable arms 38 having a plurality of electrodes 34 in a square-like or "X"-shaped configuration. Each electrode 34 may include a projecting fin as shown, which provides a heat sink into the circulating blood or fluid passing by the array 36. The electrode array 36 may be adjusted to transition between a near-linear geometry to the "X", umbrella-like geometry shown in FIG. 4, which may aid in contacting the far wall of the left or right atrium of the heart of a patient.

Figure 5:
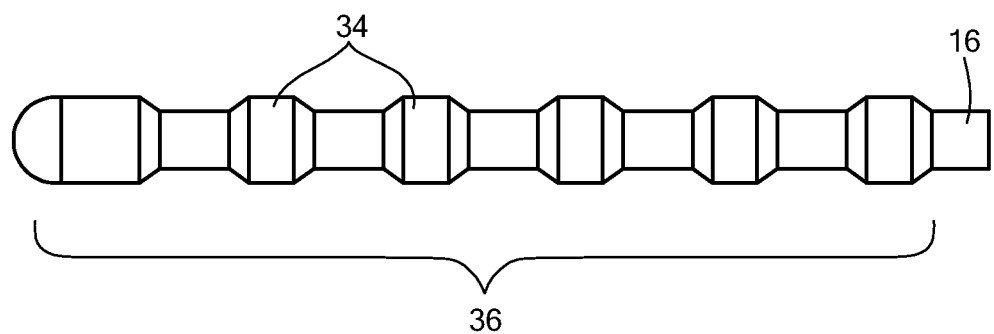
FIG. 5 is yet another illustration of an example of a medical device assembly constructed in accordance with the principles of the present invention.
Figure 6:
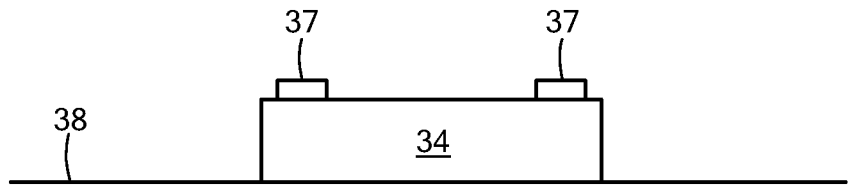
FIG. 6 is an illustration of an example of a thermocouple configuration constructed in accordance with the principles of the present invention.

Turning to FIG. 5, a plurality of electrodes 34 are shown in a substantially linear array 36 extending along a portion of the elongate body 16 of the medical device 12. Additional details related to the configurations, manipulation, and exemplary uses of the electrode configurations shown in FIGS. 2-5 are provided in U.S. patent application Ser. No. 12/116,753, filed on May 7, 2008, entitled "Ablation Therapy System and Method for Treating Continuous Atrial Fibrillation," the entirety of which is hereby incorporated by reference.

Each electrode 34 may be electrically coupled to an output portion of a radiofrequency signal generator, and each electrode 34 may also include a sensor, such as one or more thermocouples (as described herein), an electrical conductivity sensor, a spectrometer, a pressure sensor, a fluid flow sensor, a pH sensor, and/or a thermal sensor (not shown) coupled to or in communication with the electrodes. The sensors may also be in communication with a feedback portion of the control unit 14 to trigger or actuate changes in operation when predetermined sequences, properties, or measurements are attained or exceeded.

Referring again to FIG. 1, the medical device 12 may include a handle 40 coupled to the proximal portion of the elongate body 16. The handle 40 can include circuitry for identification and/or use in controlling of the medical device 12 or another component of the system. Additionally, the handle 40 may be provided with a fitting 42 for receiving a guide wire that may be passed into the guide wire lumen 24.

The handle 40 may also include connectors 44 that are matable to the control unit 14 to establish communication between the medical device 12 and one or more components or portions of the control unit 14.

The handle 40 may also include one or more actuation or control features that allow a user to control, deflect, steer, or otherwise manipulate a distal portion of the medical device 12 from the proximal portion of the medical device 12. For example, the handle 40 may include one or more components such as a lever or knob 46 for manipulating the elongate body 16 and/or additional components of the medical device 12. For example, a pull wire 48 with a proximal end and a distal end may have its distal end anchored to the elongate body 16 at or near the distal portion 20. The proximal end of the pull wire 48 may be anchored to an element such as a cam in communication with and responsive to the lever 46. The medical device 12 may include an actuator element 50 that is movably coupled to the proximal portion of the elongate body 16 and/or the handle 40 for the manipulation and movement of a portion of the medical device 12, such as the shaft 22, and/or one or more portions of the electrode assemblies described above, for example.

The system 10 may include one or more diagnostic and/or treatment sources coupled to the medical device for use in an operative procedure, such as tissue ablation, for example. The control unit 14 may include a fluid supply 52 including a coolant, cryogenic refrigerant, or the like, an exhaust or scavenging system (not shown) for recovering or venting expended fluid for re-use or disposal, as well as various control mechanisms. In addition to providing an exhaust function for the fluid or coolant supply 52, the control unit 14 may also include pumps, valves, controllers or the like to recover and/or re-circulate fluid delivered to the handle 40, the elongate body 16, and/or the fluid pathways of the medical device 12. A vacuum pump 54 in the control unit 14 may create a low-pressure environment in one or more conduits within the medical device 12 so that fluid is drawn into the conduit(s)/lumen(s) of the elongate body 16, away from the distal portion 20 and towards the proximal portion 18 of the elongate body 16. One or more valves, controllers, or the like may be in communication with one or more sensor(s) to provide for the controlled dispersion or circulation of fluid through the lumens/fluid paths of the medical device 12. Such valves, controllers, or the like may be located in a portion of the medical device 12 and/or in the control unit 14.

The control 14 unit may include a radiofrequency generator or power source 56 as a treatment or diagnostic mechanism in communication with the electrodes 34 of the medical device 12. The radiofrequency generator 56 may have a plurality of independently-operable output channels, with each channel coupled to an individual electrode 34. The independent control of each output channel allows unique (independent) closed loop power delivery, such as power delivery regulated by tissue temperature information received from one or more temperature sensors integral to the attached medical device(s) and/or from sensors included in a separate device.

The radiofrequency generator 56 may be operable in one or more modes of operation, including for example: (i) bipolar energy delivery between at least two electrodes on the medical device within a patient's body, (ii) monopolar or unipolar energy delivery to one or more of the electrodes 34 on the medical device 12 within a patient's body and through a patient return or ground electrode (not shown) spaced apart from the electrodes 34 of the medical device 14, such as on a patient's skin for example, and (iii) a combination of the monopolar and bipolar modes.

The system 10 may further include one or more sensors to monitor the operating parameters throughout the system, including for example, pressure, temperature, flow rates, volume, power delivery, impedance, or the like in the control unit 14 and/or the medical device 12, in addition to monitoring, recording or otherwise conveying measurements or conditions within the medical device 12 or the ambient environment at the distal portion of the medical device 12. The sensor(s) may be in communication with the control unit 14 for initiating or triggering one or more alerts or therapeutic delivery modifications during operation of the medical device 12. The control unit 14 may include one or more controllers, processors, and/or software modules containing instructions or algorithms to provide for the automated operation and performance of the features, sequences, calculations, or procedures described herein.

For example, each channel of the radiofrequency generator or power source 56 may utilize independent PID loops which process temperature information (e.g. temperature information received from one or more thermocouples 37 mounted on, in or otherwise coupled to each electrode 34) to modify energy delivery to that channel and/or signal an operational status of the system, such as an error or short circuit within the device and/or control unit. Alternatively or additionally to the direct electrode placement, one or more arms of the electrode array 36 may include one or more thermocouples along its length, such as midway between two electrodes. Placement of the thermocouple(s) in or on the electrode may be elected such that during operation of the electrodes, thermocouples are located directly over a target tissue at a distance separated by the electrode wall thickness only (such as a wall thickness of 0.006" or alternatively a wall thickness ranging from 0.004" to 0.010"). The combination of thermocouple location, size and mounting methods may provide improved tissue/electrode interface temperatures. In a particular example, Type T thermocouples (copper/constantan) may be employed as the temperature accuracy curve for type T is essentially linear within the temperature range used by a medical diagnosis and/or treatment system, i.e., between body temperature and approximately 80° C. The control unit may include one or more amplifiers, filters, A/D converters, microprocessors and/or other processing components in communication with the thermocouples 37 and the radiofrequency generator 56 to facilitate temperature-feedback control of the system. Additional details regarding temperature-feedback operation of radiofrequency generators are provided in application Ser. No. 12/117,596, entitled "RF Energy Delivery System and Method," filed on May 8, 2008, the entirety of which is hereby incorporated by reference.

Figure 7:
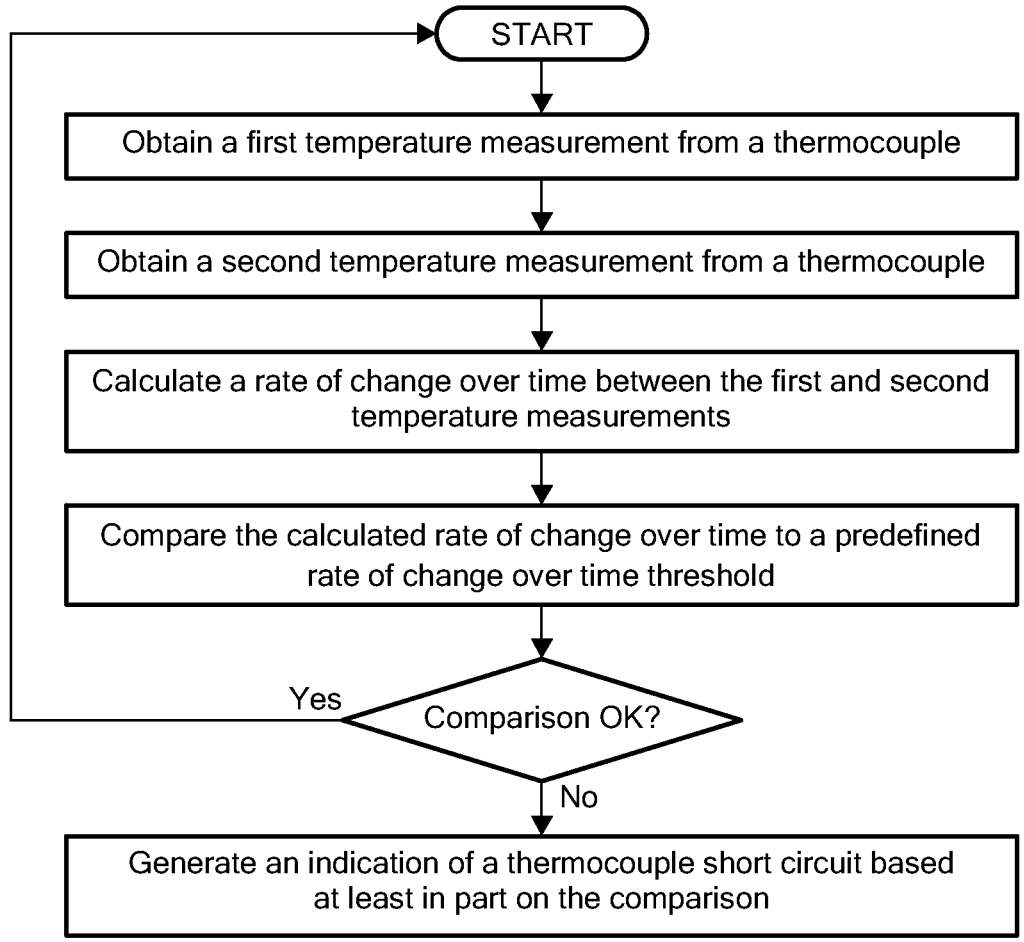
FIG. 7 is a flow chart illustrating an exemplary method of use of a medical system in accordance with the principles of the present invention.

In addition or alternatively to temperature-feedback control or modulation of the system, information or signals from the thermocouples 37 may also be used to indicate or detect a short circuit or channel fault within the control unit 14 or the medical device 12. Now turning to the flow chart of FIG. 7, an exemplary method is shown for detecting and indicating a thermocouple short circuit or channel fault in conjunction with treatment or diagnosis of a tissue site through operation of the medical device 12 and the control unit 14. In particular, the medical device 12 may be positioned adjacent a tissue site, and one or more electrodes 34 may be operated to deliver electrical and/or thermal energy to the tissue site. During operation of the one or more electrodes 34, a plurality of temperature measurements may be obtained from the thermocouple(s) 37 paired with each electrode. In particular, a first temperature measurement from a thermocouple 37 may be obtained, and a second temperature measurement may subsequently be obtained from the same thermocouple 37.

For example, the second temperature measurement sampling may occur within approximately 200 milliseconds or less of the first temperature measurement. The temperature measurements may be obtained through communication between the thermocouple and the control unit 14, and may include one or more processing, filtering, and/or calculation steps performed by one or more respective components in the control unit 14. The control unit 14 may then calculate a rate of change over time between the first and second temperature measurements, e.g., degree of temperature change per unit of time. The control unit 14 then compares the calculated rate of change over time to a predefined rate of change over time threshold. If the calculated rate of temperature per unit time is greater than the predefined threshold, which may be for example, approximately 15 degrees per second or more, then the change in temperature is more likely to be the result of a short circuit or fault in the particular thermocouple rather than a change in the physiological conditions surrounding the medical device 12 and/or electrode 34, and accordingly, then the control unit 14 will generate an indication of a thermocouple short circuit based at least in part on the comparison. The generated indication may include any one of an audible, visual, or tactile alert.

For example, measurements may be taken from the thermocouple between approximately 6 to 12 times per second (e.g., approximately every 85 to 165 ms). If there is a rapid temperature change, such as approximately 20 degrees or more, between one or two measurements, the change is likely to be the result of a short, and an indication will be generated.

The above-described methodology and processing may be performed for each individual thermocouple 37 and/or each electrode 34 of the medical device. The process may be performed repeatedly throughout the use of the medical device to provide current, real-time monitoring of the operation of the medical device 12. Calculation and comparison of the temperature rate of change over time may also be compounded with one or more measurements or indications to generate an indication of a short circuit or channel fault.

For example, a temperature rate of change over time with respect to one thermocouple 37 may be compared to or assessed in conjunction with an absolute temperature measurement of a second thermocouple, which may be coupled to the same electrode 34 as the first thermocouple. For example, a temperature measurement of the first thermocouple may be compared to a temperature measurement of a second thermocouple, and if the difference between the two measurements is less than a predefined threshold, it may be more likely that the physiological changes around the medical device are causing the temperature conditions, and an indication of a short circuit will not be generated. Alternatively, if the difference between the two measurements between the two thermocouples is too great, and indication of a short circuit will be generated. For example, if the temperature rate of change for the first thermocouple is above 15 degrees per second, and the difference in temperature between the first and second thermocouples is greater than 20 degrees, an indication will be generated.

In addition and/or alternatively to calculating a difference between the two temperature measurements, either measurement may simply be compared to a temperature threshold to determine whether or not to generate an indication of a channel fault or short circuit with respect to the thermocouple. For example, if the temperature rate of change for the first thermocouple is above 15 degrees per second, and either the first or second thermocouple is indicating a temperature greater than 60° C., an indication will be generated.

The control unit 14 and/or medical device 12 may initiate further action upon detecting a short circuit or channel fault. For example, the control unit 14 may modify and/or terminate energy delivery to the particular electrode 34 associated with the thermocouple 37 indicating a short circuit.

It will be appreciated by persons skilled in the art that the present invention is not limited to what has been particularly shown and described herein above. In addition, unless mention was made above to the contrary, it should be noted that all of the accompanying drawings are not to scale. Of note, the particular rates of change and threshold temperatures provided herein are merely examples. A variety of modifications and variations are possible in light of the above teachings without departing from the scope and spirit of the invention, which is limited only by the following claims.

What is claimed is:

1. A method of detecting a thermocouple short circuit in a medical device, comprising:
   providing a medical device having a plurality of electrodes and at least two thermocouples coupled to each electrode;
   delivering energy to each of the plurality of electrodes;
   obtaining a first temperature measurement from a first thermocouple of the at least two thermocouples of each electrode;
   obtaining a second temperature measurement from the first thermocouple of the at least two thermocouples of each electrode;
   obtaining a third temperature measurement from a second thermocouple of the at least two thermocouples of each electrode;
   comparing the third temperature measurement to a predefined temperature threshold;
   calculating a rate of change over time between the first and second temperature measurements;
   comparing the calculated rate of change over time to a predefined rate of change over time threshold; and
   generating an indication of a thermocouple short circuit when the calculated rate of change over time exceeds the predefined rate of change over time threshold,
   the indication of a thermocouple short circuit being generated based at least in part on a result of the comparison of the third temperature to the predetermined threshold.

2. The method of claim 1, wherein the second temperature measurement is obtained within approximately 200 milliseconds or less of the first temperature measurement.

3. The method of claim 1, wherein the predefined rate of change over time threshold is approximately 15 degrees per second or more.

4. The method of claim 1, wherein the energy includes at least one of radiofrequency energy, cryogenic energy, and microwave energy.

5. The method of claim 1, wherein the generated indication includes at least one of an audible, visual, and tactile alert.

6. The method of claim 1, further comprising modifying the energy delivery based at least in part on the comparison.

7. A medical treatment system, comprising:
   a medical device having a plurality of electrodes, and at least two thermocouples in proximity to each electrode;
   a control unit coupled to the plurality of electrodes and the at least two thermocouples, the control unit programmed to:
      obtain a first temperature measurement from a first thermocouple of the at least two thermocouples of each electrode;
      obtain a second temperature measurement from the first thermocouple;
      obtain a third temperature measurement from a second thermocouple of the at least two thermocouples of each electrode;
      calculate a rate of change over time between the first and second temperature measurements;
      compare the calculated rate of change over time to a predefined rate of change over time threshold;
      compare the third temperature measurement to at least one of the first temperature measurement and the second temperature measurement; and
      generate an indication of a thermocouple short circuit based at least in part on at least one of the comparison between the calculated rate of change over time and the predefined rate of change over time threshold and the comparison between the third temperature measurement and at least one of the first temperature measurement and the second temperature measurement.

8. The system of claim 7, wherein the control unit is further programmed to:
   calculate a temperature difference between the third temperature measurement and at least one of the first temperature measurement and the second temperature measurement; and
   compare the calculated temperature difference to a predetermined temperature difference threshold, the indication of a thermocouple short circuit is generated when the calculated temperature difference exceeds the predetermined temperature difference threshold.

9. The system of claim 7, wherein the control unit is programmed to:
   deliver energy to the electrode; and
   modify the energy delivery based at least in part on the comparison.

10. The system of claim 9, wherein modifying the energy delivery includes terminating energy delivery to at least one electrode.

* * * * *